(12) United States Patent
Strobel

(10) Patent No.: US 6,613,738 B1
(45) Date of Patent: Sep. 2, 2003

(54) **CYCLIC LIPOPEPTIDE FROM *CRYPTOSPORIOPSIS QUERCINA* POSSESSING ANTIFUNGAL ACTIVITY**

(75) Inventor: Gary A. Strobel, Bozeman, MT (US)

(73) Assignee: HMV Corporation, Alpine, UT (US)

( * ) Notice: Subject to any disclaimer, the term of this patent is extended or adjusted under 35 U.S.C. 154(b) by 0 days.

(21) Appl. No.: 09/856,985

(22) PCT Filed: Aug. 10, 1999

(86) PCT No.: PCT/US99/18053

§ 371 (c)(1), (2), (4) Date: May 30, 2001

(87) PCT Pub. No.: WO00/09735

PCT Pub. Date: Feb. 24, 2000

Related U.S. Application Data

(60) Provisional application No. 60/095,905, filed on Aug. 10, 1998.

(51) Int. Cl.$^7$ .......................... A61K 38/00; A61K 38/12
(52) U.S. Cl. .............................. 514/9; 514/17; 530/317; 424/405
(58) Field of Search ................................ 424/405, 780; 514/9, 17; 530/317; 435/71.3, 134, 119, 171

(56) References Cited

U.S. PATENT DOCUMENTS 5,386,010 A * 1/1995 Balkovec
5,387,670 A * 2/1995 Roy et al.
5,428,009 A * 6/1995 Hammond

FOREIGN PATENT DOCUMENTS

WO    WO 82/00587    * 3/1982

OTHER PUBLICATIONS

Noble et al. Mycol. Res. 1991. vol. 95, No. 12, pp. 1439–1440.*
Nobel, et al., "An echinocandin from an endophytic *Cryptosporiopsis sp. and Pezicula sp. in Pinus sylvestris and Fagus sylvatica.*", Mycol. Res. 1991, vol. 95., No. 12 pp. 1439–1440.

* cited by examiner

Primary Examiner—Christopher R. Tate
(74) Attorney, Agent, or Firm—McDermott, Will & Emery

(57) ABSTRACT

A unique lipopeptide antimycotic, termed Cryptocandin, is described from *Cryptosporiopsis* cf *quercina,* an endophytic fungus. Cryptocandin with a molecular mass of 1079 contains equimolar amounts of 1,2-dihydroxy-homotyrosine, 4-hydroxy proline, threonine, glutamine, 3-hydroxy-4-hydroxy methyl proline, 4,5 dihydroxy ornithine, and palmitic acid. Cryptocandin is chemically related to well-known antimycotics, the echinocandins, and pneumocandins which are produced by such fungi as *Zalerion arboricola,* Pezicula spp., and Aspergillus spp. Cryptocandin has minimum inhibitory concentration values less than 0.03 $\mu g \, ml^{-1}$ against isolates of *Candida albicans, Trichophyton mentagrophytes* and *Trichophyton rubrum.* Cryptocandin is also active against a number of plant pathogenic fungi including *Sclerotinia sclerotiorum* and *Botrytis cinerea.*

15 Claims, 5 Drawing Sheets

CYCLIC LIPOPEPTIDE FROM CRYPTOSPORIOPSIS QUERCINA POSSESSING ANTIFUNGAL ACTIVITY

This application is a 371 of PCT/US99/18053, filed Aug. 10, 1999, which claims priority to Provisional application Serial No. 60/095,905, filed Aug. 10, 1998.

TECHNICAL FIELD

The present invention is related to the isolation of an antimycotic compound. The present invention is also related to an antimycotic composition comprising the compound, and a method for controlling or treating fungal infection, particularly in humans and plants.

BACKGROUND ART

Human and plant infections caused by pathogenic fungi are a continuing and serious problem. Thus, the discovery and characterization of novel, effective antimycotics is especially important. In the case of humans, the increase in fungal infections has resulted, in part, from the frequent use of antibacterial compounds, which enhances opportunities for fungal infections. Furthermore, there is a worldwide increase in the number of immunocompromised patients who are susceptible to fungal infections. This patient population has resulted from the AIDS epidemic, chemotherapy of cancer patients, and the profusion of organ transplant patients (Miller et al., 1998).

*Cryptosporiopsis* cf. *quercina* is the imperfect stage of *Pezicula cinnamomea,* a fungus commonly associated with hardwood species in Europe (Sutton, 1980). This fungus and related species occur as endophytes and plant pathogens in many parts of the world (Sutton, 1980). Certain Pezicula spp. and *Zalerion arboricola* produce one or more members of a family of antimycotics, (lipopeptides) known as the pneumocandins. Related lipopeptides, the echinocandins, are also produced by Aspergillus species.

A fungus taxonomically related to *C.* cf *quercina* was isolated as an endophyte from *Tripterigeum wilfordii,* a medicinal plant belonging to the family Celastraceae that is native to Eurasia. Extracts of the culture medium of this fungus demonstrated excellent antifungal activity, especially to *Candida albicans* and Trichophyton spp.

DISCLOSURE OF THE INVENTION

The present application provides spectroscopic, chemical, structural, and biological evidence for the existence of a potent new antifungal agent, Cryptocandin, produced in cultures of *C.* cf *quercina.* The bioactivity of this agent indicates that it would be useful clinically for the treatment of a variety of mycoses.

The new antimycotic, Cryptocandin, appears to be another member of the growing family of aromatic lipopeptide antifungal agents having such important members as echinocandin and pneumocandin whose chemical derivatives are already in advanced human trials. Cryptocandin is indicative of a therapeutic agent as given by its impressive MIC values against *C. albicans* and *H. capsulatum* (Table 5). However, given the MIC values against Trichophyton spp. with only the mini prep C-18 Cryptocandin, it is seen that this compound has enormous potential for the control of skin and nail diseases in humans caused by Trichophyton spp. (Table 4). The results, using Cryptocandin on nail and skin infections with human volunteers have shown promising results.

Structurally, Cryptocandin has the unique aspect of having several amino acids possessing two hydroxy functionalities, and glutamine bearing none (FIG. 5), whereas pneumocandin and echinocandin have each amino acid hydroxylated (Walsh 1992). It may also be the case that other Cryptocandins occur that differ from each other by virtue of the lipid side chain. This is also a feature with other bioactive bacterially-derived lipopeptide antimycotics (Miller et al., 1998; Ballio et al., 1994).

Given the general antimycotic activity of Cryptocandin and the endophytic nature of *C.* cf *quercina,* if cryptocandin is produced in the plant, it may provide protection to the plant from invading pathogens (Table 6). This may happen at an extremely localized cellular level given how sparse endophytes can tend to be relative to the large number of cells in the plant.

As used herein, the term "Cryptocandin" includes antimycotic lipopeptide compounds found in Cryptosporiopsis. Cryptocandin is preferably a circular aromatic lipopeptide containing several amino acid residues. Preferably, the number of amino acid residues is 4 to 10. More preferably, the number of amino amino acid residues is 4 to 8. Most preferably, the number of amino acid residues is six amino acids. Also most preferably, Cryptocandin comprises equimolar amounts of 1,2-dihydroxy-homotyrosine, 4-hydroxy proline, threonine, glutamine, 3-hydroxy-4-hydroxy methyl proline, 4,5-dihydroxy ornithine, and a lipid. The lipid is preferably a fatty acid. It will be recognized that the invention can be practiced with a Cryptocandin that has been derivatized with any compound so long as the Cryptocandin maintains antimycotic properties.

As for the amino acid content of the lipopeptide of the invention, various ways of classifying the amino acids on the basis of their side groups have been proposed. The most meaningful is based on their polarity. There are four main classes of amino acids: those with (1) nonpolar or hydrophobic side groups, (2) neutral (uncharged) polar side groups, (3) positively charged side groups, and (4) negatively charged side groups (at pH 6.0 to 7.0, the zone of intracellular pH) (Lehninger, *Biochemistry,* 1982).

The six amino acid-membered Cryptocandin of the invention includes a lipopeptide described by Formula I, in which position 1 ($X_1$) can be any amino acid or its derivative, but preferably has an uncharged polar side group, and more preferably is glutamine or a derivative of glutamine, and most preferably, the glutamine is not hydroxylated. Position 2 ($X_2$) can be filled with any amino acid, but is preferably, an amino acid having a nonpolar hydrophobic side group, more preferably, a proline or a derivative of proline, and is most preferably, 3-hydroxy-4-hydroxy methyl-proline. Position 3 ($X_3$) can be filled with any amino acid or its derivative, but is preferably, an amino acid with positively charged basic side groups, more preferably, it is ornithine or its derivative, and most preferably, it is 4,5-dihydroxy ornithine. Position 4 ($X_4$) can be filled with any amino acid or its derivative, but is preferably an amino acid with uncharged polar side groups, more preferably, it is threonine or its derivative. Position 5 ($X_5$) can be filled with any amino acid or its derivative, but is preferably, an amino acid having a nonpolar hydrophobic side group, more preferably, it is proline or its derivative, and most preferably, it is 4-hydroxy-proline. Position 6 ($X_6$) can be filled with any amino acid or its derivative, but it is preferably, an amino acid with uncharged polar side groups, more preferably it is tyrosine, most preferably, it is 3,4-dihydroxy-homotyrosine. The "R" group in Formula I can be a lipid, or preferably, fatty acid.

As used herein, "derivatives" of the amino acids include any chemical modification, and preferably, but not limited to hydroxylation.

Formula I

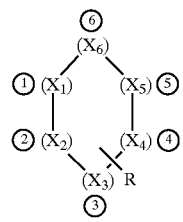

As used herein, "lipids" include fats and fat-derived materials, including, but not limited to, fatty acid esters, fatty alcohols, sterols and waxes, so long as they can be linked to the lipopeptide of the invention.

As used herein, "fatty acids" include saturated and unsaturated carboxylic acid derived from or contained in an animal or vegetable fat or oil. The fatty acids of the invention are composed of a chain of alkyl groups containing at least 4 carbon atoms, preferably up to 22 carbon atoms. Preferably, the fatty acid is palmitic acid.

Saturated fatty acids include, but are not limited to, butyric ($C_4$), lauric ($C_{12}$), myristic ($C_{14}$), palmitic ($C_{16}$), and stearic ($C_{18}$) and all of their hydroxylated derivatives. Unsaturated fatty acids include, but are not limited to, oleic, linoleic, and linolenic (all $C_{18}$).

The fatty acid can be inserted anywhere in the cyclic aromatic lipopeptide. Preferably, the fatty acid is bound to the amino acid at the third position. More preferably, the fatty acid is bound to a nitrogen atom. Most preferably, the fatty acid is bound to the nitrogen atom of a side group.

It will be recognized that the Cryptocandin compound of the present invention can be mixed, bound or associated with any other compound or composition or carrier to form a pharmaceutical composition that can be administered to a person suffering from fungal infection in any method to alleviate, treat or control the infection. Such method includes, but is not limited to, intravenous, intradermal, intramuscular, or topical administration. The effective concentration of the compound of the invention for treating fungal infection can be from about 0.1 to 5 mg per kilogram body weight.

It will be further recognized that the Cryptocandin compound can be formulated into composition that is suitable for treating or controlling plants with fungal infection.

These and other objects of the invention will be more fully understood from the following description of the invention, the referenced drawings attached hereto and the claims appended hereto.

BEST MODE FOR CARRYING OUT THE INVENTION

Figure 1A:
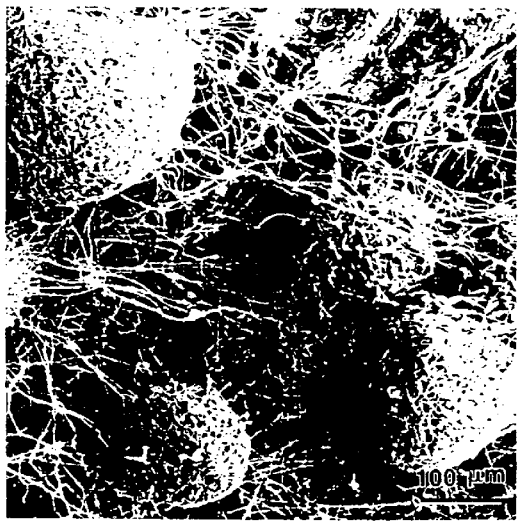
FIG. 1 A,B, conidiomata of *C*. cf. *quercina* produced on sterile carnation leaves; C, conidiophores with conidia of *C*. cf *quercina*; D, conidia of *C*. cf *quercina*.

The following examples are offered by way of illustration of the present invention, and not by way of limitation.

EXAMPLE 1

Fungal Isolation and Inoculation

Fungi were isolated from plant stems that were ca. 1.0 cm in diameter by 15 cm in length. The stem was surface treated with 70% ethanol, the outer bark removed with a sterilized sharp blade, and the pieces of inner bark/phloem/cambium tissues plated on water agar in Petri plates. After several days incubation at 23° C., individual hyphal tips of the developing fungal colonies were removed and placed onto potato dextrose agar (PDA), incubated for 8–10 days, and periodically checked for culture purity. Eventually, pure cultures were transferred again, by hyphal tipping, to Petri plates containing water agar with small pieces of sterilized carnation leaves and incubated an illuminated incubator cycling 12 h light and 12 h dark at 18° C. The gamma-irradiated leaves commonly encourage the development of fungal fruiting structures which aid in their identification. The fungal isolate of interest was numbered and stored in distilled water at 4° C. as agar plugs in PDA slants covered with mineral oil at 23° C., and in 15% (v/v) glycerol at −70° C. as spores and mycelium. The fungus identified as *Cryptosporiopsis* cf. *quercina* was deposited October, 1998 in the Montana State University culture collection and assigned Accession No. 2039.

EXAMPLE 2

Fungal Identification by Microscopy

Fungal spores and fruiting bodies appearing on the carnation leaf fragments were examined by stereo and light microscopy for measurement and identification. Reference strains from the Centraalbureau voor Schimmelcultures (CBS), Baarn, The Netherlands, were used for comparison. Comparisons of the culture characteristics were made by standard methods after growing the organisms on PDA at 23° C. Fruiting structures were fixed and processed using the methods of Upadhyay et al., 1991, except that they were placed in 2% (v/v) glutaraldehyde in 0.1 M sodium cacodylate buffer (pH 7.2). The samples were critical point dried, gold coated with a sputter coater and observed and photographed with a JEOL 6100 scanning electron microscope. Assistance in fungal identification was also provided by Dr. R. A. Samson of the CBS.

EXAMPLE 3

Cryptocandin Isolation Procedures

Small agar blocks containing the fruiting structures and mycelia of *C*. cf *quercina* were inoculated into 1000 ml of MID culture medium (Pinkerton & Strobel, 1976) and incubated for 3 weeks at 22° C. The mat that developed was blended along with the broth in an equal volume of 95% ethanol. The mixture was gently shaken overnight and the insoluble materials removed by centrifugation at 10,000×g for 10 min. The supernatant fluid was taken to dryness by flash evaporation. Fifty ml of methanol was added to the dry residue. After thorough stirring, the methanol soluble extract was taken to dryness by flash evaporation and the residue redissolved in 1000 ml of H$_2$O. This solution was passed over an Amberlite XAD-2 column (2.5×30 cm) and then rinsed with 500 ml of isopropanol:H$_2$O 20:80 (v/v), followed by 300 ml of a 30:70(v/v) mixture of the same solvents. Finally, the column was eluted with 800 ml of a mixture of a 50:50 (v/v) isopropanol:H$_2$O and the solution taken to dryness by flash evaporation. The residue (20 mg) was dissolved in 4 ml of 25% (v/v) acetonitrile in water and placed on a preconditioned (pre-washed with methanol and 25% acetonitrile) Alltech Altima mini C-18 column with 300 mg of resin. After loading, this column was washed with 3 to 4 ml of 25% acetonitrile in H$_2$O and finally eluted with 75% acetonitrile in H$_2$O. The eluate was taken to dryness by flash evaporation. Final separation (0.2–0.3 mg per run) was accomplished by high performance liquid chromatography (HPLC) on an Altima C-18 column (7.8×250 mm; Alltech) and eluted with a linear gradient of 25–100% acetonitrile in H$_2$O over 35 min at 3 ml/min (method 1). The eluate was monitored at 208 nm and fractions were assayed for their activity against *C. albicans*. Other elution methods included a 45–100% acetonitrile:H$_2$O linear gradient (method 2), and a 0–100% gradient of solvent A, 50:50 methanol:H$_2$O (v/v), and solvent B, 75:25 acetonitrile: isopropanol (method 3).

EXAMPLE 4

Bioassays

To demonstrate the general antifungal activity of *C. cf quercina*, known weights of semi-purified (mini C-18 column) preparations were placed on PDA plates and overlaid with the test organism in 0.4% agar. These tests were conducted with various plant pathogenic fungi, certain human pathogenic fungi, and isolates of Trichophyton spp. However, a purified preparation (final HPLC methods 1–3) of Cryptocandin was used for determination of minimal inhibitory concentrations. These determinations were done on several selected and commonly occurring fungal pathogens using the microbroth dilution assay as recommended by the Subcommittee on Antifungal Susceptibility Testing of the U.S. National Committee for Clinical Laboratory Standards (NCCLS). Appropriate controls were run concomitantly along with the known antifungal agents echinocandin B and amphotericin B. Simple bioassays were conducted on various extracts and column effluents via spotting 10–20 μl of solvent on PDA plates, drying the agar surface under a hood, and overlaying plates with a suspension (10$^4$–10$^6$ spores ml$^{-1}$) of *C. albicans*. Bioactivity was recorded as the diameter of the zone of inhibition that resulted (Miller et al., 1998).

EXAMPLE 5

Amino Acid Analysis

Lyophilized HPLC-purified compounds were dissolved in 50% methanol in water, placed in 6×50 mm glass tubes, dried in vacuo and then placed in a hydrolysis cylinder (Millipore part no. 007603). Approximately 300 μl of 6 N HCl (Pierce Chemical Co.) were added to the cylinder, which was then alternately purged with nitrogen and evacuated three times before being sealed under vacuum. Vapor phase hydrolysis was performed by heating at 110° C. for 22 h. After cooling, the cylinders were dried in vacuo, opened, the residue in each tube dissolved in 2% sodium citrate buffer (pH 2·0) and then analyzed using a Beckman Model 6300 Amino Acid Analyzer (Miller et al. 1998). Ninhydrin—positive peaks were detected both at 570 and 440 nm. Comparative analyses were also performed on echinocandin and pneumocandin and Cryptocandin. With the exceptions of glutamine and threonine, an absolute determination of all residues in Cryptocandin was not possible given the unavailability of these amino acids standards.

EXAMPLE 6

Fungal Strains

All fungi used for test purposes for sensitivity to Cryptocandin were obtained from the American Type Culture Collection and the mycological collection at Montana State University (Bozeman, Mont., USA), Eli Lilly Co., Indianapolis, Ind., and Dr. Mike Rinaldi's lab of the University of Texas Health Science Center, San Antonio, Tex. 78284.

Mass spectroscopic analysis. Cryptocandin, derivatized Cryptocandin, and methylated amino acids obtained after hydrolysis of Cryptocandin (see preparation of chemical derivatives) were each subjected to electrospray mass spectroscopy analysis by dissolving the sample in methanol: water: acetic acid (50:50:1, v/v/v). The samples were injected into Montana State University's custom-built instrument with a spray flow of 2 μl min$^{-1}$ and a spray voltage of 2·2 kV via the loop injection method.

EXAMPLE 7

Nuclear Magnetic Resonance Spectroscopy

Nuclear magnetic resonance (NMR) spectroscopy was applied on Cryptocandin and other compounds in a Brucker 500 MHz instrument with the sample dissolved in 100% deuterated methanol. Each sample was subjected to 2048 scans with a sweep width of 6024 and 8 k real points.

EXAMPLE 8

Thin Layer Chromatography

All comparative TLC analyses were carried out on Merck 0.25 mm silica gel plates developed in the following solvents: A) n-butanol: pyridine: acetic acid: H$_2$O (15:10:3:12, v/v/v/v); B) methylene dichloride: methanol: acetic acid: H$_2$O (8:2:0.5:0.5, v/v/v/v); C) n-butanol: picoline: acetic acid: H$_2$O (15:10:3:12, v/v/v/v); and D) chloroform: acetonitrile: acetic acid: H$_2$O: methanol (7:3:0.5:1:2, v/v/v/v/v). Compounds were detected by a spray reagent consisting of 1% vanillin (w/v) with sulfuric acid after gentle heating (Cardellina, 1991) or with a 0.5% ninhydrin ethanolic solution with gentle heating, or by viewing under short wave UV light (ca. 254 nm).

EXAMPLE 9

Preparation of Chemical Derivatives

Methylation of lipopeptides as well as free amino acids was carried out using standard procedures. The methylation reagent was prepared first by the careful addition of acetyl chloride (160 μl) with stirring, to 1 ml of methanol over a course of 5 min. Then 50–100 μl of the methylation reagent was incubated with 10–15 μg of peptide or amino acid mixture for 1–2 hr. The sample was ultimately blown dry under a stream of N$_2$ gas and redissolved in 10 μl of methanol for mass spectral analysis. This procedure effectively methylates acidic carbon atoms in peptides and in free amino acids.

4,4'Dimethoxytrityl chloride (DMT) was used as a check for the presence of primary alcohol functionalities in Cryptocandin with various standard peptides, lipopeptides, and amino acid controls (Tuschl et al., 1993). The reaction was carried out by dissolving the anhydrous amino compound (100 μg) in 50 μl of pure anhydrous pyridine. Then, an approximate equal molar amount of DMT was then added with stirring. After 2 hr of incubation at 23° C., the excess pyridine was removed under a stream of $N_2$ gas. About 50 μl of methanol was added to quench the unreacted DMT and the methanol and pyridine were removed under a stream of $N_2$ gas. The products of this reaction were separated by TLC in solvent system D. The separated products were detected on the plates by blowing a steady stream of trifluoroacetic acid vapors onto the plate. The reaction products turn yellowish-orange immediately.

All solvents used for TLC and HPLC were HPLC grade. Those used for extraction were ACS grade. All other reagents were obtained from Sigma, St. Louis, Mo. Standard echinocandin B and pneumocandin L 748-842 were generous gifts of Eli Lilly Co., Indianapolis, Ind. and Merck Co., Rahway, N.J., respectively.

EXAMPLE 10

Identification of The Fungal Endophyte

Figure 1B:
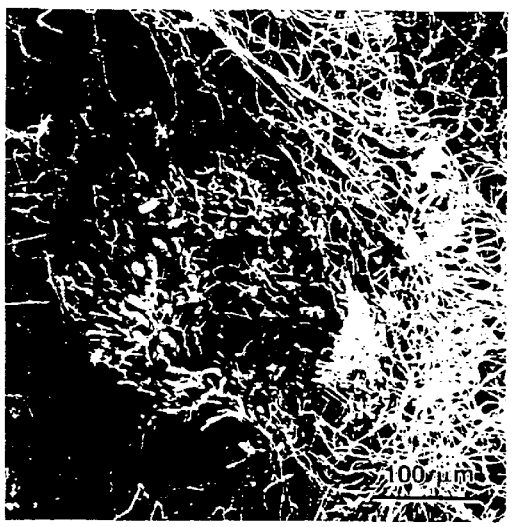
Figure 1C:
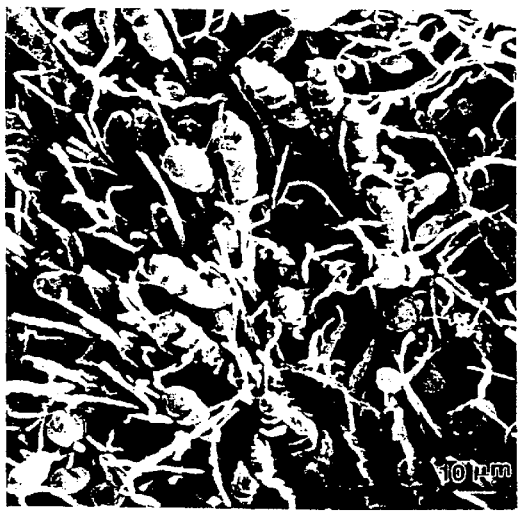
Figure 1D:

Although stems of *T. wilfordii* yielded a number of endophytic fungi, the fungus of greatest interest best answered to the description of *Cryptosporiopsis* cf *quercina*. The conidiomata typically were 250–300 μm when the fungus was grown on sterile carnation leaves, but ones as large as 500–1000 μm were also noted (FIGS. 1A–B). The conidia were comparatively large, 19–25×8.5–9.7 μm, hyaline, thin walled, smooth, ellipsoid with an obtuse apex. The base of each spore tapered to a very distinct truncate scar (FIGS. 1C–D). The conidiogenesis cells appeared to vary in length from 30–40 μm, and 1.4–1.6 μm in dia (FIG. 1C–D). Overall, this fungus differs primarily from the exact description of *C.* cf *quercina* in the diameter of the conidiogenous cells being 3–4 μm as well as in the diameter of the conidia as described by Sutton (1980). Furthermore, although cross walls in conidia are not shown by Sutton (1980) in Cryptosporiopsis spp., they do appear to be present in this organism (FIG. 1D). They may have been missed, because of the hyaline nature of the conidia. Nevertheless, *C.* cf *quercina* is the name tentatively adopted for this fungus. This appears to be the first mention of any Cryptosporiopsis spp. from a Celastraceous plant.

EXAMPLE 11

Purification of Cryptocandin

Figure 2:
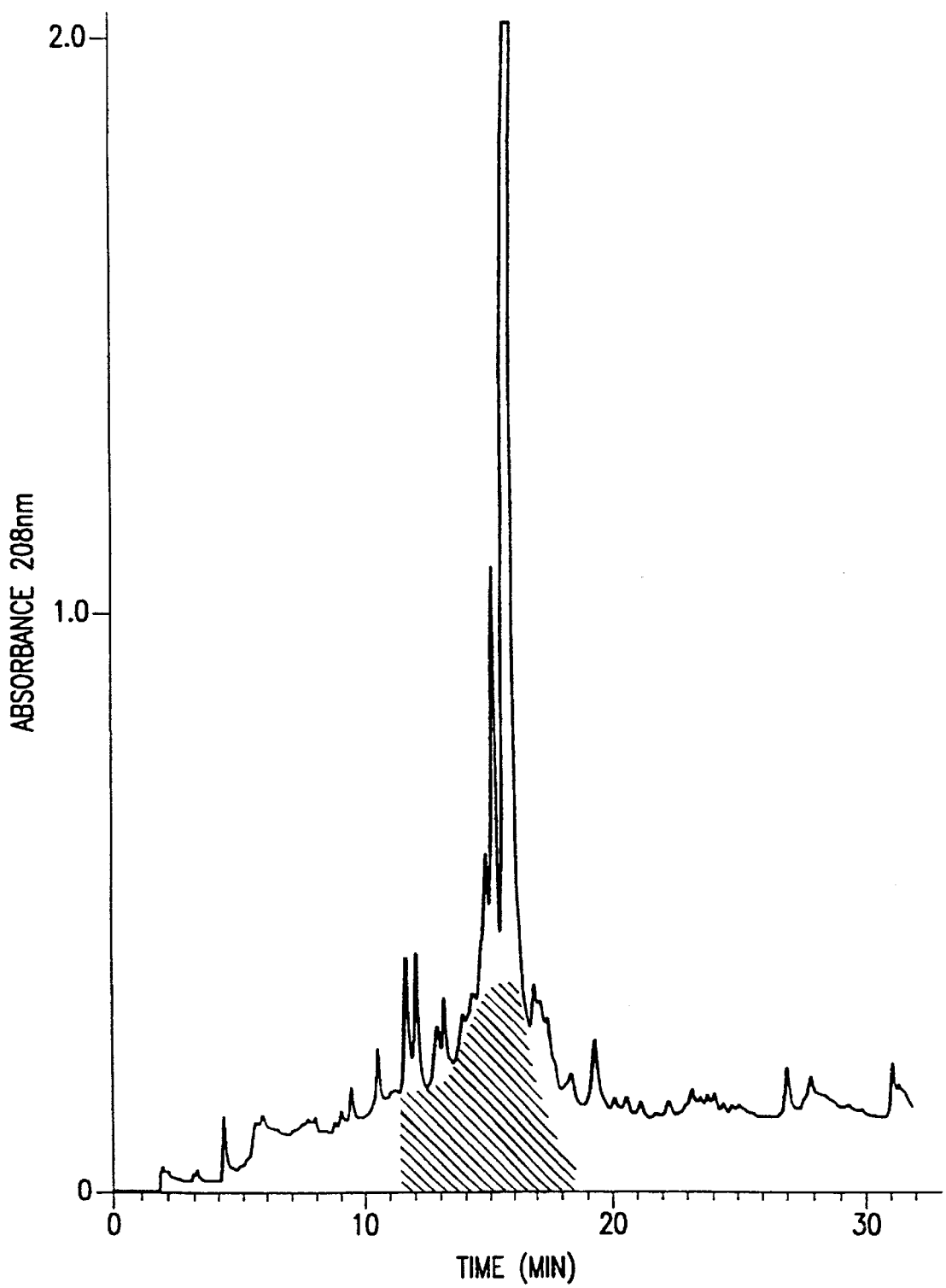
FIG. 2 Elution profile of the antifungal extract of *C*. cf *quercina* from an Altima C-18 HPLC column. The column was monitored at 208 nm and each fraction was checked for antifungal activity against *Candida albicans*. The main peak at 14–17 min possessed the antifungal activity (shaded area). The elution time was 3 ml min$^{-1}$ using solvent system (1) (see Materials and Methods).

One major peak of antimycotic activity appeared in the effluent of the HPLC-Altima C-18 column between 14 and 17 min (FIG. 2) when 200–300 μg of the material from the C-18 column was injected into it. A sample (10 μl) from the peak eluting at 15–16 min produced a 22 mm zone of inhibition in the *C. albicans* bioassay test. The eluate between 14 and 17 min was pooled, taken to dryness by flash evaporation, and successively passed through the C-18 column using methods 2 and 3, successively. Method 3 yielded a single peak that was identical to the major peak in method 1 (14–17 min) (FIG. 2). The final product was checked by TLC in solvent systems A, C, and D and shown to yield a single UV absorbing spot under the shortwave UV light, a reddish-brown reaction product with the vanillin-sulfurin acid reagent, and a weak yellowish-pink spot with ninhydrin. The compound was considered homogenous and the fungus yielded up to 3–4 mg/1000 ml of culture medium.

EXAMPLE 12

Spectroscopy of Cryptocandin

Several spectroscopic evaluations helped confirm the relative purity of the Cryptocandin-antimycotic preparation. Electrospray mass spectroscopy revealed an $[M+H]^+$ peak at 1080.6 and $[M+Na]^+$ at 1102.7 with no other contaminating peaks. Thus, the apparent mass of Cryptocandin is 1079.6. Cryptocandin possessed UV absorption maxima at 233 and 273 with millimolar extinctions of 2.7 and 1.9, respectively. The $^1H$ NMR spectrum of Cryptocandin was substantially free of signals of contamination (FIG. 3) and it, along with other spectroscopic data, suggested that Cryptocandin was an aromatic-lipopeptide. Previously described aromatic lipopeptides possessing antimycotic activity include families of echinocandins and pneumocandins (Dictionary of Natural Products 1996). Therefore, in order to distinguish Cryptocandin from the other aromatic lipopeptides, both analytical and spectroscopic chemical studies were conducted.

EXAMPLE 13

Comparative TLC Studies

The $R_F$ values of echinocandin B, pneumocandin L 748-842 and Cryptocandin illustrated that Cryptocandin differs from these earlier established structures (Table 1). The occurrence of two spots, instead of one, in solvent system B with both echinocandin B and Cryptocandin may occur as a result of the racemization of the dihydroxy ornithine residue. Each compound absorbed in the short wavelength UV range, each gave a yellowish-pink spot with ninhydrin and each produced a reddish-brown spot with the vanillin-sulphuric acid reagent.

EXAMPLE 14

Constituent Residues of Cryptocandin

The fatty acid content of Cryptocandin was determined after methylation of samples followed by gas chromatography/mass spectroscopy (Alltech). Cryptocandin possessed a fatty acid whose retention time and spectral characteristics were identical to methyl palmitate. This is in contrast to pneumocandin A whose fatty acid moiety is dimethylmyristate and echinocandin B, having linoleic acid as a fatty acid moiety. Several other fatty acids also occur as side chains on the family of echinocandins and pneumocandins (Directory of Natural Products 1996).

Figure 4:
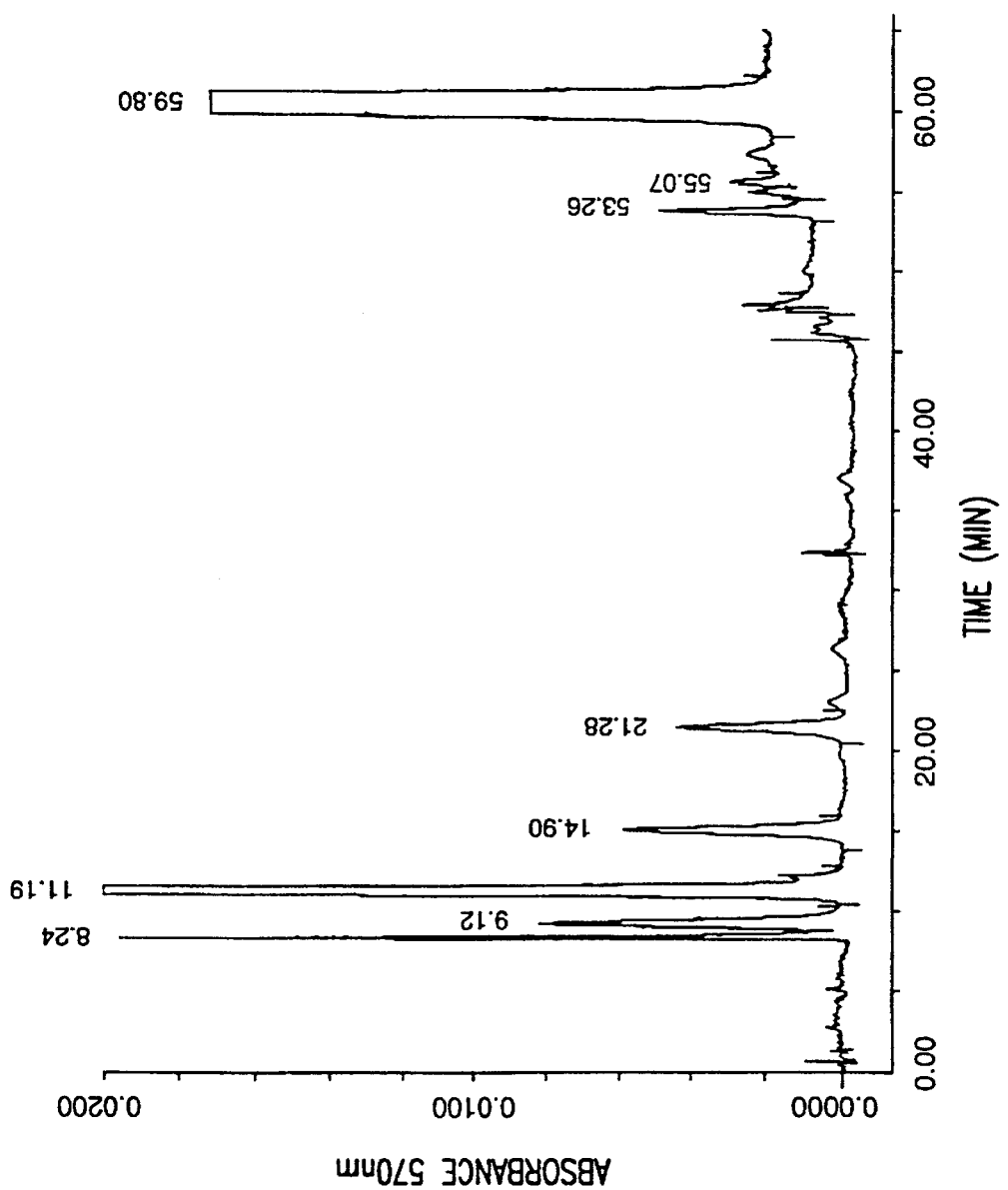
FIG. 4 Amino acid elution profile of the acid hydrolyzate of Cryptocandin. Detection of column effluent was at 570 nm for the ninhydrin reaction products.
Figure 5:
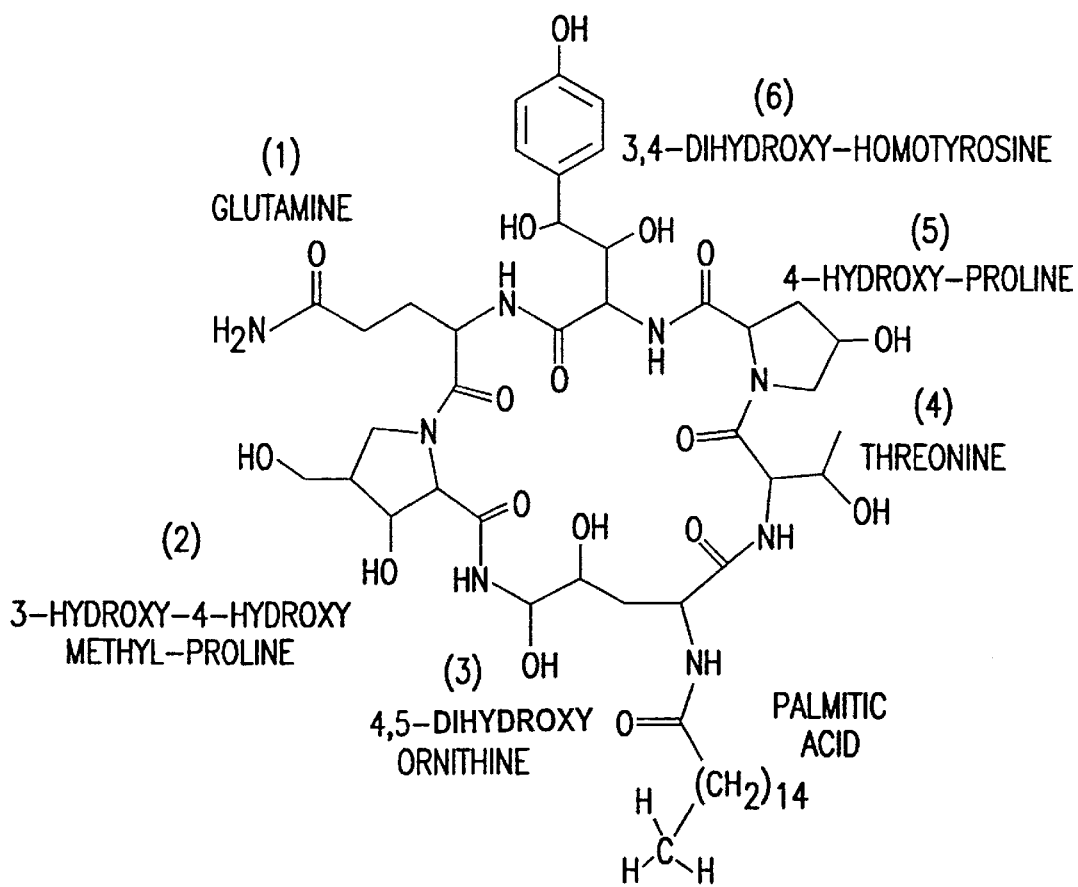
FIG. 5 Proposed structure of a preferred embodiment of Cryptocandin (no stereochemistry is implied).

Amino acid analysis of Cryptocandin showed that it contained residues of threonine, 4-hydroxy-proline, 3,4-dihydroxy-ornithine and 4,5-dihydroxy-ornithine. These amino acid residues eluted from the analytical column at 11.19, 9.12, 21.28, and 53.26–55.07 min, respectively (FIG. 4). Threonine and 4-hydroxy proline eluted at times identical to authentic standards. Identities of the other two residues, were inferred from comparison of retention times with those amino acids derived by hydrolysis of echinocandin B, which produced peaks with identical retention times as 4,5 dihydroxy-ornithine and 3,4 dihydroxy-homotyrosine. The former amino acid residue typically appears as multiple peaks as a result of racemization which occurs around the hydroxy-aminal functional group and the adjacent carbon on position number 4 and 5 (FIG. 5). Additional evidence for the identity of these amino acids, was, in part, provided by electrospray mass spectroscopy of the methylated mixture derived from the hydrolyzate of Cryptocandin (Table 2).

The remaining peaks at 14.90 and 8.24 min did not occur in the hydrolyzates of either echinocandin B or pneumocandin L 748-842, suggesting major structural differences between these molecules and Cryptocandin. Since pneumocandin A° and Cryptocandin possess the same molecular weight, and since at least 4 of the amino acid residues are identical, the other two must therefore, be different.

Electrospray mass spectroscopy of the methylated Cryptocandin revealed an [M+H]$^+$ peak at 1108.2 suggesting Cryptocandin had been di-O-methylated (1079+14+14+1= 1108). Interestingly, echinocandin B also methylates (Rodriguez, Eli Lilly Co.) on both the acidic phenyl hydroxy and hydroxy aminal groups on 3,4-dihydroxy-homotyrosine and 4,5-dihydroxy-ornithine, respectively. Thus, neither of the two remaining amino acid residues in Cryptocandin could have either free carboxyl or acidic OH groups as potential sites of methylation. One peak in the amino acid profile had the identical retention time as glx (glutamic acid/glutamine) at 14.90 min (as compared to authentic glutamic acid) (FIG. 4). Furthermore, a compound with a mass identical to the di-O-methylester of glutamic acid appeared in the methylated hydrolate of Cryptocandin (Table 2). Therefore, the peak at 14.9 min must represent glutamine since Cryptocandin would have been triply methylated if free glutamic acid were present.

The remaining amino acid residue with a retention of 8.24 min on the amino acid column (FIG. 4) produced a methyl ester with an observed mass of 162. We suggest that this compound may be dihydroxy methyl proline. This amino acid residue, along with 4-hydroxy-proline produced a yellowish ninhydrin product when the amino acid analytical column was monitored at 440 nm. Furthermore, a prolyl-like residue is normally conserved in this group of substances (Dictionary of Natural Products 1996).

Figure 3:
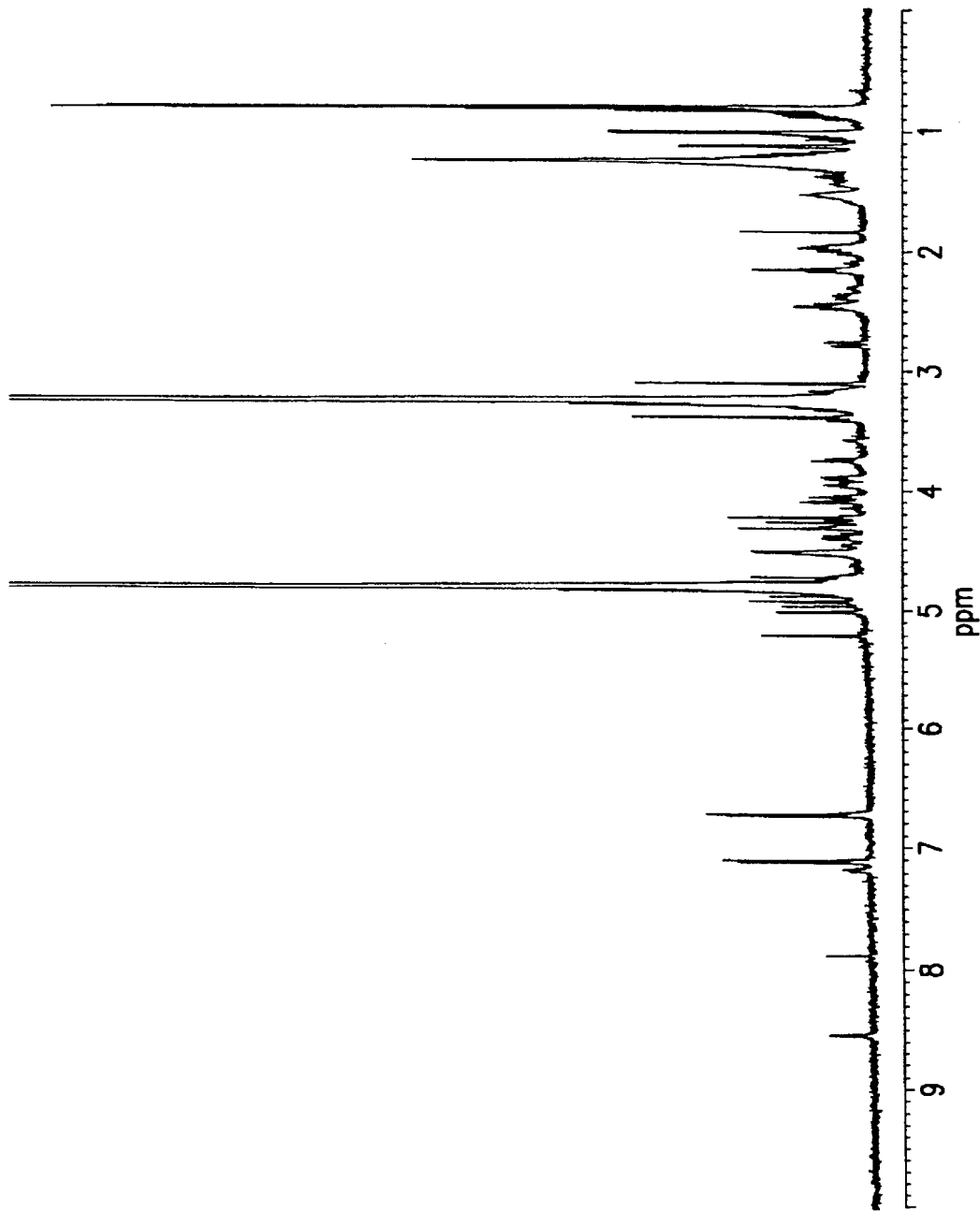
FIG. 3 A $^1$H-NMR spectrum of Cryptocandin taken in 100% deuterated methanol.

If this residue is a dihydroxymethyl proline residue, it represents the only residue in Cryptocandin with a primary alcohol functionality. As such, it would be expected to produce reaction product with the DMT reagent and the electrospray mass spectrum of the reaction products yielded an expected peak with an [M+H+H]$^{++}$ of 692 (Table 3). A whole series of peptides, lipopeptides and amino compounds with and without primary alcohol functionalities were also checked for their reactivity with this reagent and the products separated by TLC solvent D (Table 3). Pneumocandin L 748-842, pseudomycin or other peptides not possessing a primary hydroxyl were not reactive with DMT, but other peptides were reactive (Table 3). Likewise, as expected, serinol, with 2 primary alcohols, produced two reaction products with DMT (Table 3). Although each of the residues is accounted for, bringing the total mass of Cryptocandin to 1079, the position of the hydroxyl groups on dihydroxy methyl proline are unknown. At this point, we suggest that the structure of this residue is 3-hydroxy -4-hydroxy methyl-proline based on the 3,4 substitutions on this residue that occurs on all other known pneumocandins, and echinocandins (Walsh, 1992). Therefore, with no stereochemistry implied, the proposed structure of Cryptocandin shows similarity to the other known compounds (FIG. 5). Typically, the order of amino acids in these molecules is conserved with the exception of position ① wherein compounds with serinyl, threonyl, or hydroxy glutaminyl substitutes at this position have been described (Walsh 1992). Also, we have inferred the sequence of these amino acids, based on the striking similarities between the NMR spectra of Cryptocandin and echinocandin (FIG. 3). Other compounds with varying degrees of hydroxylation at positions ③ and ⑥ are also known and several have been described with demethylation at position ② (FIG. 5). However, a compound with glutamine at position ① and dihydroxy methyl proline at position ② has not been previously described (Dictionary of Natural Products 1996). Furthermore, Cryptocandin appears to be structurally distinct from the echinocandins and pneumocandins in that one of its amino acids (glutamine) lacks a hydroxyl functionality. As a result of these subtle, structural changes, the Cryptocandin molecule exhibits unique biological activities.

EXAMPLE 15

Biological Activities of Cryptocandin

The most impressive antifungal activity of Cryptocandin (mini C-18 preparation) was on Trichophyton spp. (Table 4). The minimum inhibitory concentrations (MIC) of 0.035–0.07 µg/ml were observed for various isolates of *Trichophyton rubrum*, as well as *Trichophyton mentagraphtes* (Table 4).

MIC values for purified Cryptocandin were also acquired for a series of some of the most important fungal pathogens of humans (Table 5). The most impressive activity was against *C. albicans* at 0.02 µg/ml and *Histoplasma capsulatum* at 0.01 µg/ml. These data are virtually identical to those obtained for amphotericin B, the most common clinically used antifungal agent (Table 5). However, with echinocandin B the MIC on *Candida albicans* was just 0.3 µg/ml (Table 5). Cryptocandin had little effect on both *Aspergillus fumigatus* and *Cryptococcus neoformans*, in contrast to amphotericin B (Table 5).

Mini C-18 column preparations of Cryptocandin were examined for their effects against a wide array of plant pathogenic fungi with the most notable susceptible organism, in these tests, being *S. Sclerotiorum* (Table 6). However, many of the other organisms tested showed little, no, or weak susceptibility to the Cryptocandin preparation.

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

REFERENCES

Ballio, A., Bossa, F., Collina, A., Gallo, M., Iacobellis, N. S., Paci, M., Pucci, P., Scaloni, A., Segre, A. & Simmaco, M. (1990). Structure of syringotoxin, a bioactive metabolite of *Pseudomonas syringae* p.v. *syringae*. *FEBS Lett* 269, 377–380.

Ballio, A., Baara, D., Bossa, F., Collins, A., Grgurina, I., Mario, G., Moneti, G., Paci, M., Pucci, P., Segre, A. & Simmaco, I. (1991). Syringopeptins, new phytoxic lipodepsipeptides of *Pseudomonas syringae* p.v. *syringae*. *FEBS Lett* 291, 109–112.

Ballio, A., Bossa, F., DiGiorgio, D., Fenanti, P., Paci, M., Pucci, P., Scaloni, A., Segre, A. and Strobel, G. A. (1994). Novel bioactive lipodepsipeptides from *Pseudomonas syringae:* the Pseudomycins. *FEBS Lett* 355, 96–100.

Cardellina, J. H. (1991). HPLC separation of taxol and cephalomannine. *J Chromatogr* 14, 659–665.

Dictionary of Natural Products on CD ROM 1996 Chapman and Hall Electronic Publishing Division. London (updated biannually).

Miller, C. M., Miller, R. V., Garton-Kenny, D., Redgrave, B., Sears, L. J., Condron, M. M., Teplow, D. B. & Strobel, G. A. (1998). Ecomycins, unique antimycotics from *Pseudomonas viridiflava*. *J Appl Microbiol* 84, 937–944.

Nelson, P. E., Tousson, T., and Morasas, W. F. O. (1983). Fusarium species. Pennsylvania State University Press; University Park, Pennsylvania.
Pinkerton, F. & Strobel, G. A. (1976). Serinol as an activator of toxin production in attenuated cultures of *Helminthosporium sacchari*. Proc Natl Aca Sci USA 73,4007–4011.
Segre, A., Bachmann, R. C., Ballio, A., Bossa, F., Grgurina, I., Iacobellis, N. S., Marino, G., Pucci, P., Simmaco, M. and Takomoto, J. Y. (1989). The structure of syringomycins A, E and G. *FEBS Lett* 255, 27–31.
Strobel, G. A. & Long, D. M. (1998). Endophytic microbes embody pharmaceutical potential. *ASM News* 64, 263–268.
Sutton, B. C. (1980). *The Coelomycetes*. Commonwealth Mycological Institute: Kew.
Tuschl, T., Ng, M. M., Pieken, W., Benselu, F. & Eckstein, F. (1993). Importance of exocyclic base functional groups of central core guanosines for hammerhead ribozyme activity. *Biochemistry* 32, 11658–11668.
Upadhyay, R. V., Strobel, G. A. & Hess, W. M. (1991). Morphogenesis and ultrastructure of the conidiomata of *Ascochyta cypericola*. *Mycol Res* 95, 785–791.
Walsh, T. A. (1992). Inhibitors of β glucan synthesis. In Emerging Targets in *Antibacterial and Antifungal Chemotherapy*, pp. 349–373. Edited by J. A. Sutcliffe & N. H. Georgopapadakou. London, Chapman & Hall.
Schwartz, R. E. et al., J. Antibiot., (1989), 42, 163, 168, 174, 1992, 45, 1853, 1867, 1875, 1886, 1953
Adefarati, A. A. et al., *J.A.C.S.*, (1991), 113, 3542
Noble, H. M. et al., *Mycol. Res.*, (1991), 95, 1439
U.S. Pat. No. 5,021,403 (1991)
Schwartz, R. E. et al., *Clin. Dermatol*, (1993), 7, 375
Bartizal, K. et al., *Clin. Dermatol.*, (1993), 7, 421
Morris, S. A. et al., *J. Antibiot.*, (1994), 47, 755
Benz, F. et al., *Helv. Chim. Acta*, (1974), 57, 2459
Keller-Juslen, C. et al., *Tet. Lett.*, (1976). 4147
Ger. Pat. 2,643,485 (1977)
U.S. Pat. No. 4,024,245 (1977)
Traber, R. et al., *Helv. Chim. Acta*, (1979), 62, 1252
U.S. Pat. No. 4,288,549 (1981)
U.S. Pat. No. 4,293,419 (1981)
U.S. Pat. No. 4,293,483 (1981)
U.S. Pat. No. 4,293,489 (1981)
Iwata, K. et al., *J. Antibiot.*, (1982), 35, 203, 210
U.S. Pat. No. 4,320,053 (1982)
Evans, D. A. et al., *J.A.C.S.*, (1987), 109, 7151
Kurokawa, N. et al., *Tetrahedron*, (1993), 49, 6195
Japan, Pat. 76 98 387 (1976)
Mizuno, K. et al.,*J. Antibiot.*, (1977), 30, 297
Satoi, S. et al., *J.Antibiot.*, (1977), 30, 303
Canadian Pat. 1 041 446 (1978)
Mukhopadhyay, T. et al., *J. Antibiot.*, (1987), 40, 275, 281
Mukhopadhyay, T. et al., *J. Antibiot.*, (1992), 45, 618
Japan, Pat. 76 98 387 (1976)
Mizuno, K. et al.,*J. Antibiot.*, (1977), 30, 297
Canadian Pat. 1 041 446 (1978)
Mizuno, K. et al.,*J. Antibiot.*, (1977), 30, 297
Satoi, S. et al., *J.Antibiot.*, (1977), 30, 303
Canadian Pat. 1 041 446 (1978)
Lewis, R. J., *Sax's Dangerous Properties of Industrial Materials*, 8$^{th}$ edn., Van Nostrand Reinhold, (1992), AEC625

TABLE 1

Comparative thin layer chromatography $R_F$ values of Cryptocandin, echinocandin and pneumocandin L748-842 in solvents A–D. Details of the solvent systems, separations and detection schemes are given in the Materials and Methods

| Compound | Solvent System $R_F$ | | | |
|---|---|---|---|---|
| | A | B | C | D |
| Cryptocandin | 0.72 | 0.17–0.12* | 0.66 | 0.15 |
| Echinocandin B | 0.81 | 0.27–0.22* | 0.76 | 0.26 |
| Pneumocandin | 0.59 | 0.35 | 0.56 | 0.01 |

*Each of these compounds produced secondary ghost spots in solvent B which may result from the racemization of dihydroxy-omithine.

TABLE 2

Methylation of the hydrolysis products of Cryptocandin and subjection of the mixture to electrospray mass spectroscopy. The calculated $[M + H]^{50}$ for the amino acids found in Cryptocandin are indicated along with the $[M + H]^+$ observed for each of the amino acids.

| Methylated Amino Acid Residue | Molecular Weight +H$^+$ | |
|---|---|---|
| | Calculated | Observed |
| 1,2-dihydroxy-homo tyrosine (dimethyl) | 242.21 | — |
| 4-hydroxy proline (methyl) | 146.15 | 146.30 |
| Threonine (methyl) | 134.14 | 134.40 |
| Glutamic acid (dimethyl) | 176.16 | 176.10 |
| 3-hydroxy-4-hydroxy methyl proline (methyl) | 162.18 | 162.20 |
| 4,5 dihydroxy ornithine (dimethyl) | 193.19 | 192.90 |

TABLE 3

DMT derivatization of Cryptocandin and other peptides followed by TLC in solvent system D. Detection was done by exposing the dried plate over a vapour of trifluoroacetic acid.

| DMT derivative of Peptide/Compound | $R_F$ Value* |
|---|---|
| Cryptocandin | 0.76 |
| Pseudomycin | no product |
| Echinocandin B | 0.46, 0.34** |
| Pneumocandin | no product |
| Serinol | 0.41, 0.69 |
| arg-lys-asp-tyr (Sigma A-4777) | no product |
| trp-ala-gly-gly-asp-ala-ser-gly-glu (Sigma 1762) | 0.07 |
| ala-leu-ill-leu-thr-leu-val-ser (Sigma 1061) | 0.04 |
| asp-ser-asp-pro-arg (Sigma 3526) | 0.04 |

*No DMT products were formed with peptides or lipopeptides lacking a primary alcohol functionality. The source of the peptides is listed by their Sigma catalog numbers.
**Echinocandin produced at least two DMT derivatives due its degradation resulting in products with primary alcohols (Dictionary of Natural Products 1996).

TABLE 4

Minimum Inhibitory Concentrations (MIC's) of Cryptocandin (mini C-18 column preparation) against Trichophyton isolates*

| Species | Isolate Number | Plate MIC (ng)** |
|---|---|---|
| *T. mentagrophytes* | ATCC 28185 | 70 |
| | 7P-1796 | 35 |
| | 7P-1797 | 35 |
| | 8P-1027 | 70 |

TABLE 4-continued

Minimum Inhibitory Concentrations (MIC's) of Cryptocandin (mini C-18 column preparation) against Trichophyton isolates*

| Species | Isolate Number | Plate MIC (ng)** |
|---|---|---|
| *T. rubrum* | ATCC 28188 | 70 |
|  | 7P-1794 | 35 |
|  | 7P-1801 | 35 |
|  | 7P-1803 | 35 |
| *Candida albicans* (control) | ATCC 90028 | 35 |

*ATCC from American Type Culture Collection, others are clinical isolates from the laboratory of Dr. Michael Rinaldi, Fungus Testing Laboratory at the University of Texas Health Science Center at San Antonio.
**Plate MIC is the amount required to induce a visible clear zone of inhibition on a PDA plate overlaid with the test organism in 0.4% agar. Results with *C. albicans* indicate that MIC's conducted in 96 microwell plates usually require 2 to 5 fold less antifungal compound for activity (eg. *C. albicans* with a plate MIC of 35 ng had a corresponding 96 well MIC of 7 ng).

TABLE 5

Minimum inhibitory concentrations (MIC's) of Cryptocandin (purified) and other antifungal agents against various human pathogenic fungi.

| | Antifungal Agent Minimum Inhibitory Concentration ($\mu$g/ml) | | |
|---|---|---|---|
| Test Fungal Pathogens | Cryptocandin | Echinocandin B | Amphotericin B |
| *Candida albicans* | 0.03 | 0.3 | 0.04 |
| *Cryptococcus neoformans* | >20 | >20 | 0.04 |
| *Aspergillus fumigatus* | >20 | >20 | 0.03 |
| *Candida parasilopsis* | 2.5 | — | 0.01 |
| *Histoplasma capsulatum* | 0.01 | — | 0.01 |

TABLE 6

Minimum inhibitory concentration of Cryptocandin (mini C-18 column preparation) against various plant pathogenic fungi in two replicated experiments

| | 96 well MIC and Plate inhibition tests | | | |
|---|---|---|---|---|
| | Test 96 Well $\mu$g ml$^{-1}$ | | Plate Test Cryptocandin/fungus plug 25 $\mu$g applied | |
| Test fungus | (test 1) | (test 2) | (test 1) | (test 2) |
| *Geotrichum candidum* | 3.12 | 125 | none | trace |
| *Rhizoctonia solani* | 50 | 31.2 | none | none |
| *Sclerotinia sclerotiorum* | 0.78 | 15.6 | 15 mm | 15 mm |
| *Fusarium solani* | none | none | * trace | * trace |
| *Botrytis cinerea* | 6.2 | 3 | 22 mm | 22 mm |
| *Pythium ultimum* | 50 | 125 | trace | trace |
| *Ustilago hordei* | none | none | none | none |

What is claimed is:

1. A lipopeptide antimycotic compound isolated from Cryptosporiopsis, wherein said compound comprises equimolar amounts of 1,2-dihydroxy-homotyrosine, 4-hydroxy proline, threonine, glutamine, 3-hydroxy-4-hydroxy methyl proline, 4,5-dihydroxy ornithine, and a lipid.

2. A compound according to claim 1, wherein said lipid is a fatty acid.

3. A compound according to claim 2, wherein said fatty acid lipid is palmitic acid.

4. A compound according to claim 1, wherein said compound is a circular aromatic lipopeptide.

5. A compound according to claim 1, wherein said compound has a molecular weight of about 1079 Daltons.

6. An antifungal composition comprising a lipopeptide of claim 1, and an acceptable carrier therefor.

7. A composition according to claim 6, wherein said composition is mycocidally effective against Candida, or Trichophyta.

8. The composition according to claim 6, wherein said composition is mycocidally effective against plant pathogenic fungi.

9. The composition according to claim 6, wherein said composition is mycocidally effective against Scleroinia, or Botrytis.

10. An antifungal composition comprising a composition of claim 6, and a carrier therefor, for treating fungal infections in plants.

11. A method of treating fungal infections, comprising administering a fungal controlling effective amount of a composition of claim 6 to a person in need thereof.

12. The method according to claim 11, wherein said fungal infection occurs on external portion of the person.

13. The method according to claim 11, wherein said fungal infection occurs on human nails.

14. An aromatic lipopeptide comprising the following formula:

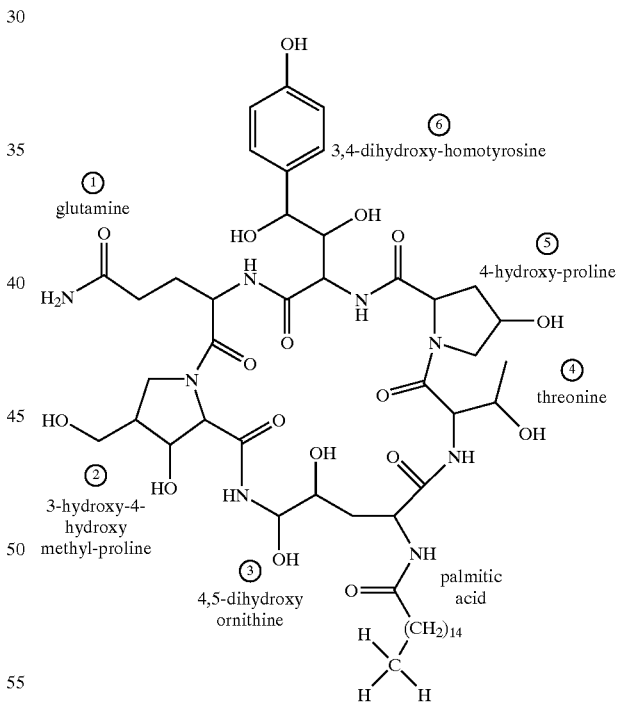

wherein ①, ②, ③, ④, ⑤ and ⑥ represent positions on the ring occupied by the named amino acids.

15. An antifungal composition comprising the lipopeptide of claim 14, and an acceptable carrier therefor.

* * * * *